United States Patent
Albanese et al.

(10) Patent No.: US 8,964,935 B2
(45) Date of Patent: Feb. 24, 2015

(54) APPARATUS FOR MAMMOGRAPHY AND/OR TOMOSYNTHESIS WITH DEVICE FOR REMOVING DIFFUSE RADIATION

(75) Inventors: Achille Albanese, Marzabotto (IT); Bruno Toniolo, Pontecchio Marconi (IT); Sara Vecchio, Casalecchio di Reno (IT); Paolo Vignoli, San Giovanni In Persiceto (IT); Giovanni Borasi, Reggio Emilia (IT)

(73) Assignee: I.M.S. Internazionale Medico Scientifica S.r.l. (IT)

( * ) Notice: Subject to any disclaimer, the term of this patent is extended or adjusted under 35 U.S.C. 154(b) by 382 days.

(21) Appl. No.: 13/401,491

(22) Filed: Feb. 21, 2012

(65) Prior Publication Data
US 2012/0219110 A1    Aug. 30, 2012

(30) Foreign Application Priority Data

Feb. 25, 2011    (IT) ............................... BO2011A0086

(51) Int. Cl.
| | |
|---|---|
| G21K 1/04 | (2006.01) |
| G21K 1/02 | (2006.01) |
| A61B 6/04 | (2006.01) |
| A61B 6/06 | (2006.01) |
| A61B 6/00 | (2006.01) |
| A61B 6/02 | (2006.01) |

(52) U.S. Cl.
CPC ................. *A61B 6/5282* (2013.01); *A61B 6/02* (2013.01); *A61B 6/502* (2013.01); *A61B 6/4291* (2013.01)
USPC .............................. 378/37; 378/154; 378/155

(58) Field of Classification Search
USPC ........... 378/4–20, 37, 62, 189, 204, 210, 154, 378/155; 250/397; 359/230–232, 613, 614, 359/641, 896
See application file for complete search history.

(56) References Cited

U.S. PATENT DOCUMENTS

| | | | | | |
|---|---|---|---|---|---|
| 2,818,510 | A | * | 12/1957 | Verse ............................. | 378/189 |
| 4,926,453 | A | * | 5/1990 | Toniolo .......................... | 378/37 |
| 5,195,120 | A | * | 3/1993 | Evain et al. .................... | 378/154 |

(Continued)

FOREIGN PATENT DOCUMENTS

| | | |
|---|---|---|
| EP | 2236087 | 10/2010 |
| WO | 2009/012453 | 1/2009 |

OTHER PUBLICATIONS

Italian Search Report dated Oct. 6, 2011 from counterpart foreign application.

*Primary Examiner* — Anastasia Midkiff
(74) *Attorney, Agent, or Firm* — Timothy J. Klima; Shuttleworth & Ingersoll, PLC

(57) ABSTRACT

An apparatus for tomosynthesis and/or mammography includes: an X-ray detector, for receiving and detecting X-rays in a first, detection plane; an X-ray source, which can be activated individually and is positioned to emit a corresponding X-ray beam towards the first, detection plane; a processing and control unit, for activating the X-ray source and receiving a signal relating to X-rays which passed through the breast and were detected by the detector to derive a radiographic image representative of the internal structure of the breast; a grille for removing diffuse radiation, interposed between the source and the detector to receive X-rays which passed through the breast. The grille including plates positioned opposite the chest of the patient when the breast is positioned in a positioning region, and which are angled to converge towards the same region proximal to the X-ray source.

14 Claims, 2 Drawing Sheets

(56) References Cited

U.S. PATENT DOCUMENTS

| | | | |
|---|---|---|---|
| 5,418,832 A * | 5/1995 | Barnes | 378/146 |
| 5,594,769 A * | 1/1997 | Pellegrino et al. | 378/37 |
| 6,054,712 A | 4/2000 | Komardin et al. | |
| 6,999,554 B2 * | 2/2006 | Mertelmeier | 378/37 |
| 2004/0228447 A1 * | 11/2004 | Dobbs et al. | 378/154 |
| 2008/0175350 A1 * | 7/2008 | MacDonald | 378/37 |
| 2009/0003519 A1 * | 1/2009 | Defreitas et al. | 378/37 |
| 2009/0135996 A1 * | 5/2009 | Muller et al. | 378/37 |
| 2009/0214130 A1 | 8/2009 | Yamakita | |
| 2009/0274272 A1 * | 11/2009 | Stanton et al. | 378/62 |
| 2010/0135456 A1 * | 6/2010 | Jing et al. | 378/22 |

* cited by examiner

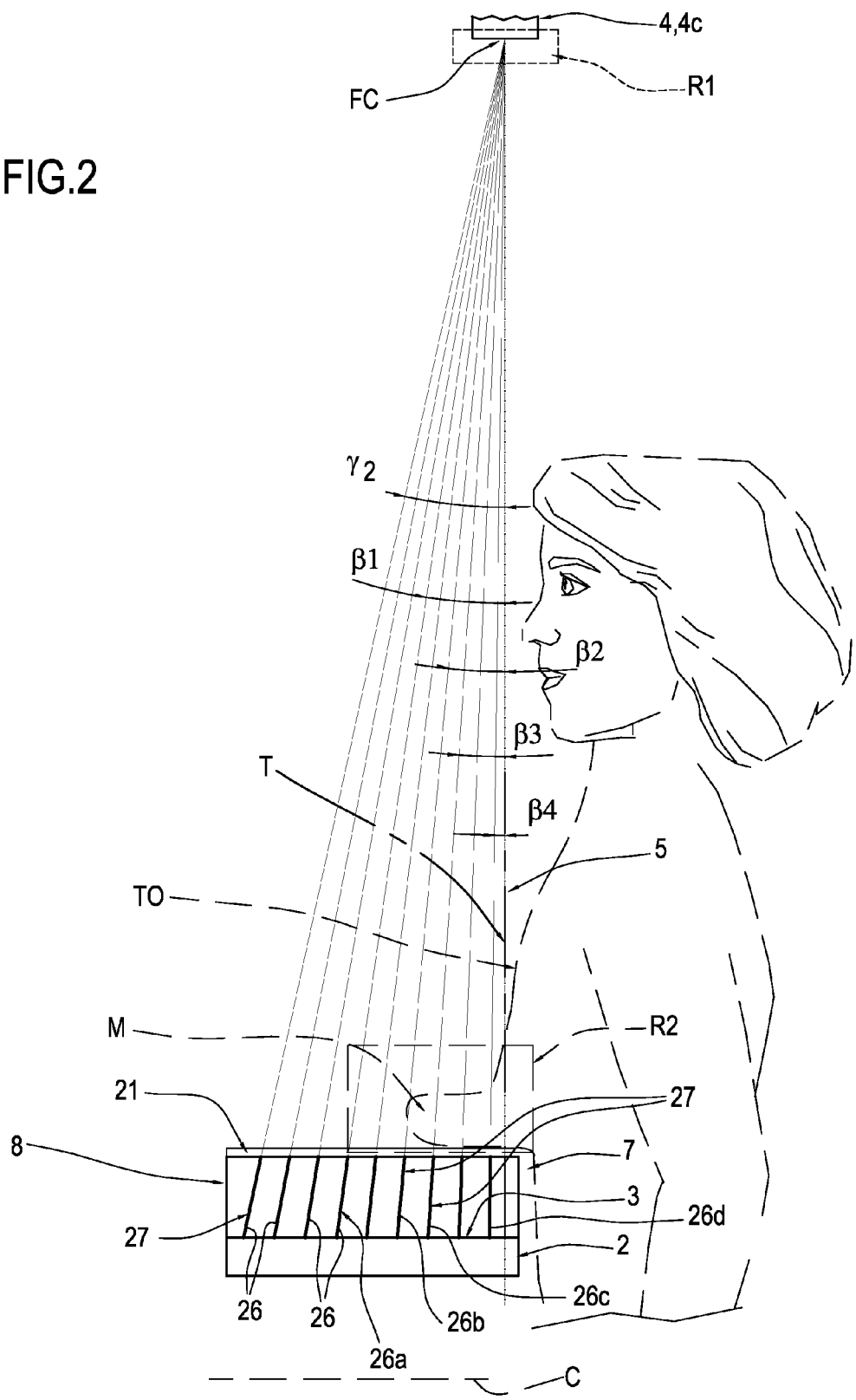

APPARATUS FOR MAMMOGRAPHY AND/OR TOMOSYNTHESIS WITH DEVICE FOR REMOVING DIFFUSE RADIATION

This application claims priority to Italian Patent Application BO2011A000086 filed Feb. 25, 2011, the entirety of which is incorporated by reference herein.

BACKGROUND OF THE INVENTION

This invention relates to an apparatus for performing mammography and/or tomosynthesis (in particular, digital breast tomosynthesis) and equipped with a device for removing diffuse radiation.

Known in the prior art are apparatuses designed to perform both digital breast tomosynthesis (DBT) and mammography.

These apparatuses comprise an X-ray source and a detector configured to receive the X-rays emitted by the source.

It should be noted that the patient's breast being analyzed is interposed between the X-ray source and the detector in such a way that the X-rays emitted by the source pass through the breast Generally speaking, the breast is placed on a suitable rest and compressed by a plate known as compressor.

As is known, in the breast being analyzed X-rays are absorbed to a different extent by parts affected by tumor growths or the like as compared to parts without tumor growths. A radiographic image obtained from the X-rays received by the detector can thus be analyzed to identify suspected tumors.

When X-rays pass through a part of the human body such as the breast, however, secondary photons are generated. These secondary photons (also known as "scattering radiation" or "diffuse radiation" or "secondary radiation") propagate in different directions relative to the rays emitted by the X-ray source (that is, relative to the radiation referred to as "primary" radiation).

This secondary radiation, if it is not adequately intercepted and attenuated, strikes the detector device together with the primary radiation and is detected by the detector device. As a result, the quality of the radiographic image obtained is appreciably poorer (loss of sharpness and contrast) on account of the noise produced by the secondary radiation.

To improve the quality of the radiographic images, these apparatuses are equipped with a system which is interposed between the breast and the detector device and which removes the diffuse radiation by collimation of the primary radiation.

An implementation typical of mammography is accomplished by a grille of plates which, in use, are arranged substantially at a right angle to the patient's chest, that is to say, in such a way that the planes defined by the large planar faces of the plates is almost at a right angle to the plane defined by the patient's chest.

This grille allows the secondary radiation incident upon the detector device to be reduced and thus improves the inherent contrast and spatial resolution of the mammographic images.

Where the X-rays are emitted from a plurality of different positions relative to the detector device, as in the case of tomosynthesis where the sources are movable relative to the detector, collimation of the primary beam would require a different orientation of the plates for each position. Vice versa, the use of a typical mammographic grille for all the tomosynthesis projections would produce the negative effect of attenuating the primary beam for each position different from the position for mammography. It should be noted that poor image quality is particularly evident at the limit positions adopted by the X-ray source relative to the detector.

To date, this problem is avoided by removing the grille when the apparatus is used for tomosynthesis.

Removal of the grille may be automated or manual.

It should be noted that if the grille has to be removed manually by the operator, the breast must be decompressed (that is, the patient must be made to move) to allow the grille to be removed. In this case, therefore, it is not possible to perform both mammography and tomosynthesis in combination while compressing the breast only once, which means that spatial adjustment of the images is more difficult and that it is impossible to save an X-ray dose as a result of using mammography as one of the projections for the tomosynthesis examination. Moreover, manual removal of the grille is awkward for the operator and for the patient. The grille must be handled with great care (to avoid damage caused if it is dropped or knocked against a hard surface).

Automated grille removal during a combined examination, on the other hand, takes some time and involves discomfort for the patient, whose breast remains compressed while waiting for the automatic system to remove the grille. Moreover, the overall dimensions of the apparatus are appreciably increased on account of the need to provide a zone where the grille can be housed when it is not operatively interposed between the breast and the detector.

A need which is strongly felt by operators in this field is that for an apparatus which can provide good quality mammographic/tomosynthesis images (that is, sharp images with a good quality contrast) during both tomosynthesis and mammography without having to remove the grille.

SUMMARY OF THE INVENTION

This invention therefore has for an aim to satisfy the aforementioned need by providing an apparatus for performing mammography and/or tomosynthesis which allows radiographic images of very good quality to be obtained.

A further aim of the invention is to provide an apparatus for performing mammography and/or tomosynthesis in which the quantity of secondary radiation incident upon the detector device is greatly reduced.

In accordance with the invention, this aim is achieved by an apparatus for performing tomosynthesis and mammography comprising the technical features set out in one or more of the appended claims.

BRIEF DESCRIPTION OF THE DRAWINGS

The technical features of the invention according to the above mentioned aims are clearly described in the claims below and its advantages are more apparent from the detailed description which follows, with reference to the accompanying drawings which illustrate a non-limiting example embodiment of the invention and in which:

FIG. 2 shows a filtering device which can be associated with the apparatus of FIG. 1 in a schematic side view according to the viewing direction J1.

DESCRIPTION OF THE PREFERRED EMBODIMENTS

Figure 1:
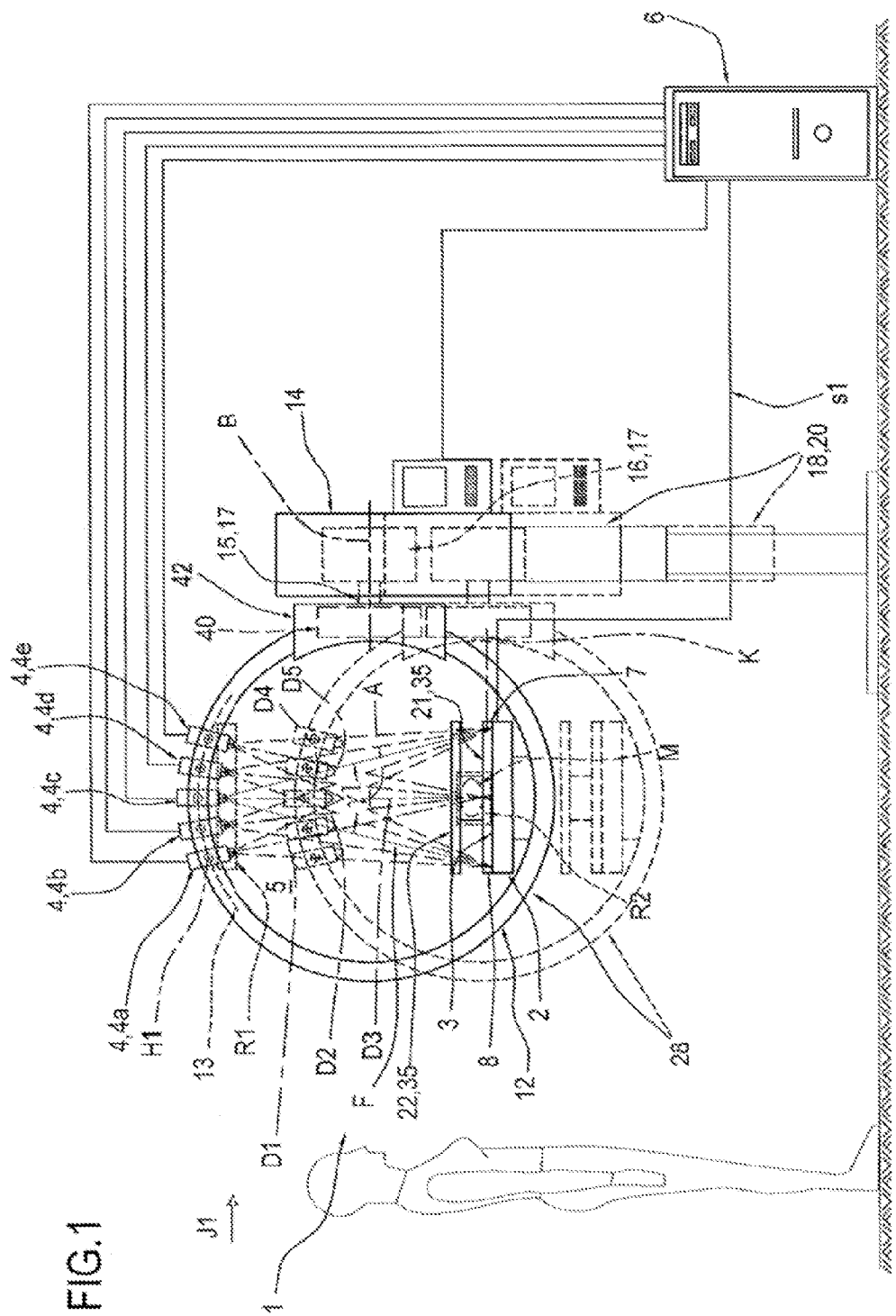
FIG. 1 is a schematic front view of a preferred embodiment of an apparatus according to this invention.

With reference to the accompanying drawings, the numeral 1 denotes an apparatus for tomosynthesis and/or mammography according to this invention.

More specifically, it should be noted that the apparatus 1 according to the invention allows mammography and/or tomosynthesis to be performed on a patient's breast.

Hereinafter, the term "patient" is used to mean a person, whether male or female, subjected to analysis using the apparatus 1.

The apparatus 1 comprises an X-ray detector device 2 designed to receive and detect X-rays in a first, detection plane 3 (hereinafter also referred to as detection plane 3).

It should be noted that the detector device 2 is a substantially two-dimensional detector.

The detector device 2 comprises a sensor designed to detect a flow of X-rays incident upon the detection plane 3.

It should be noted that preferably, but without limiting the invention, the sensor of the detector device 2 is a solid state sensor based on amorphous selenium.

The apparatus 1 comprises one or more X-ray sources 4. Preferably, the sources 4 are X-ray tubes.

It should be noted that the term "X-ray tube" or just "tube" will hereinafter be used. This term must not however be understood as limiting the scope of the invention since the X-ray tube may, in variants not illustrated, be substituted for X-ray sources of other kinds.

The X-ray sources 4 are positioned in such a way as to emit a corresponding X-ray beam F towards the first, detection plane 3.

In the embodiment illustrated in FIG. 1, the apparatus 1 comprises a plurality of X-ray tubes 4 positioned along a second plane 5.

It should be noted that, alternatively, the apparatus 1 might also comprise a single X-ray tube 4 movable in a second plane 5 relative to the detector device 2.

More generally speaking, the apparatus 1 according to the invention may comprise one or more X-ray sources 4 mounted in a chosen position relative to the detector device 2 or one or more movable X-ray sources 4 or, alternatively, any combination of X-ray sources 4 which are fixed and X-ray sources 4 which are movable relative to the detector device 2.

It should be noted that the X-ray sources 4 are oriented in such a way as to direct the X-ray beams at the detector device 2. More specifically, it should be noted that in the apparatus 1, the fixed sources 4 are positioned in the same second plane 5 and the movable sources 4 are movable in the same second plane 5 (to allow the position of the X-ray sources to be varied).

Preferably, but without limiting the invention, with reference to the embodiment illustrated in FIG. 1, the apparatus 1 comprises five X-ray tubes, which are individually labeled 4a, 4b, 4c, 4d, 4e.

The term "X-ray tube" or just "tube" is hereinafter used to refer to any generic X-ray source (that is, it is not used in a restrictive sense).

It should be noted that in FIG. 1, the beam F of X-rays emitted by the respective sources 4 is preferably a beam of slightly diverging X-rays directed principally along a corresponding principal direction of emission (D1, D2, D3, D4, D5).

Indeed, as may be observed in FIG. 1, each tube 4 emits a beam of X-rays according to an emission cone (whose opening angle, labeled γ1 in FIG. 1 and γ2 in FIG. 2, is adjustable in both directions).

In light of this, it should be noted that each X-ray tube (4a, 4b, 4c, 4d, 4e) is preferably equipped with a beam collimating device which is configured to adjust the divergence of the beam relative to the principal direction of emission (D1, D2, D3, D4, D5).

According to what is described above, the X-ray tubes (4a, 4b, 4c, 4d, 4e) are positioned in the same second plane 5.

The second plane 5 is preferably but without limiting the invention, at a right angle to the first, detection plane 3.

It should be noted that, in the embodiment illustrated, the tubes 4 are oriented, relative to the first, detection plane 3, according to a plurality of different angles, that is, the principal directions of emission (D1, D2, D3, D4, D5) differ from each other in orientation relative to the first, detection plane 3.

Each X-ray tube (4a, 4b, 4c, 4d, 4e) is, moreover, activatable individually to emit a corresponding X-ray beam F towards the first, detection plane 3.

The fact of having several tubes 4 which are angularly positioned relative to the first, detection plane 3 allows the apparatus 1 to perform tomosynthesis (where, as is known, the signal needs to be detected from a plurality of different positions/angles).

Alternatively, the apparatus 1 might also be embodied in such a way as to perform tomosynthesis with one or more tubes 4 which are movable to allow irradiation from different positions and/or different angles.

More generally speaking, the apparatus 1 comprises, for the purposes of tomosynthesis, a configuration of fixed/movable tubes 4 such that the X-rays can be generated from at least two different positions.

According to the invention, the apparatus 1 also comprises a processing and control unit 6.

The processing and control unit 6 is connected to the X-ray tubes 4 in order to activate them and is also connected to the detector device 2 in order to receive a signal s1 relating to the quantity of X-rays received by the detector device 2.

The processing and control unit 6 is designed to derive from the signal s1 received a radiographic image representative of the portion of the patient's body subjected to examination (that is, the breast).

It should be noted that the radiographic image is obtained by suitably processing the signal s1.

The apparatus 1 comprises a first frame 12 for supporting the X-ray tubes 4 and the detector device 2.

The first frame 12 has the shape of a ring. More specifically, it should be noted that in FIG. 1, the centre of the ring 28 defined by the first frame 12 is labeled A.

It should be noted that in the embodiment illustrated in FIG. 1, the detector device 2 and the stationary X-ray tubes 4 are stably fixed to the first frame 12. Thus, the stationary X-ray tubes 4 are positioned in a predetermined space relationship with the detector device 2.

It should also be noted that in the embodiment illustrated in FIG. 1, the stationary X-ray tubes are preferably supported by an arc 13 of the selfsame ring 28 defined by the first frame 12, while the device 2 is preferably, but without limiting the invention, positioned in the internal region of the ring 28 defined by the first frame 12.

It should be noted that if the apparatus 1 comprises one or more tubes 4 which are movable relative to the detector device 2, these tubes 4, too, are supported by the first frame 12 (that is, by the ring 28).

According to another aspect, the apparatus 1 further comprises a first contact element 21 configured to support the patient's breast M on it, and a second breast M contact element 22 which is movable to allow compression, or squeezing, of the breast M between the first contact element 21 and the second contact element 22 itself.

The first contact element 21 and the second 22 together define means 35 for the stable positioning of the breast M interposed between the detector device 2 and the X-ray tubes 4 to allow the breast M to be stably positioned.

It should be noted that the expression "stable positioning of the breast" used herein means the breast M is held in a desired position relative to the detector device 2 while mammography/tomosynthesis is being performed.

It should also be noted that the two elements (21, 22) define a region or zone R2 for positioning the breast (that is, a region where the breast is positioned in such a way that the X-ray beams emitted by the tubes 4 pass through it).

It should be noted that according to another aspect, the means 35 for the stable positioning of the breast M may be movable relative to the detector device 2 (that is, relative to the frame 12), in such a way that the breast can be positioned and compressed in different regions of the detector device 2.

It should also be noted that more generally speaking the positioning region R2 is a spatial region in which the breast can be positioned in such a way that the X-ray beams emitted by the tubes 4 can pass through it in order to perform mammography/tomosynthesis.

Also in the preferred embodiment, the apparatus 1 comprises a second frame 14 and the first frame 12 is rotatably supported relative to the second frame 14.

More specifically, the first frame 12 is rotatable about an axis B (preferably horizontal) parallel to the second plane 5.

It should also be noted that, in the preferred embodiment, the axis B lies in the second plane 5 and, still more preferably, passes through the centre A of the ring 28.

It should be borne in mind that advantageously rotating the ring 28 about the axis B allows mammography/tomosynthesis to be performed with the patient lying on an examination couch.

According to this aspect, the patient is preferably made to lie on her back on the examination couch and the ring 28 is rotated through approximately 90 degrees about the axis B to a predetermined position under the couch.

In FIG. 1, the reference numeral 15 denotes a mounting shaft for supporting the first frame 12 and the reference numeral 16 denotes means for rotationally driving the shaft 15, both forming part of the apparatus 1.

It should be noted that the mounting shaft 15 and the means 16 for rotationally driving the shaft 15 define means 17 for rotating the first frame 12 relative to the second frame 14.

It should also be noted that in the preferred embodiment, the first frame 12 is movable vertically relative to the second frame 14.

In effect, the second frame comprises a telescopic portion 18 whose length may be varied to allow the first frame 12 to be lifted/lowered.

The telescopic portion 18 and the related movement means (not illustrated) define means 20 for vertical movement of the first frame 12 relative to the second frame 14.

FIG. 1 shows two different vertical positions of the first frame 12, one drawn with a dashed line and the other with a continuous line.

It should be noted that in variants not illustrated, the means 20 for vertical movement of the first frame 12 relative to the second frame 14 may comprise diverse devices or means for allowing the first frame 12 to move vertically relative to the second frame 14.

It should also be noted that according to another aspect, the ring 28 is supported rotatably about its own centre A (or, more generally speaking, about an axis perpendicular to the plane 5).

In effect, it should be noted that the ring 28 is rotatably coupled to an element 42 which is integral with the shaft 15. In other words, the ring 28 is rotatable about its own centre A relative to the second frame 14.

It should also be noted that the reference numeral 40 denotes means for rotating the ring 28 about the axis A and forming part of the apparatus 1.

The rotation means 40 are associated with the element 42.

According to this aspect, it is possible to rotate the ring 28 as one about its own centre A. This rotation causes both the tubes 4 and the detector device 2 to rotate about A.

According to this aspect, it is possible to perform examinations in any of the modes allowed by the apparatus, with the ring 28 positioned at different angles of rotation about A corresponding to the breast M being compressed along different directions.

In short, it should be noted that the first frame 12 is supported rotatably by the second frame 14 about a first axis B and about a second axis A. The axes A and B are at right angles to each other.

According to the invention, the apparatus 1 comprises a grille 7 for removing diffuse radiation and which defines a device for removing diffuse radiation.

The grille 7 for removing diffuse radiation is interposed between the X-ray tubes 4 and the detector device 2, that is, it is located along the path of the X-ray beam F so as to intercept the beam F.

More specifically, while mammography and tomosynthesis are being performed (that is, during use of the apparatus 1) the grille 7 for removing diffuse radiation is interposed between the patient's breast and the detector device 2.

It should be noted that the grille 7 for removing diffuse radiation defines a space 8 for removing diffuse radiation configured to allow only X-rays having predetermined angles to pass through it.

It should be noted that hereinafter, the radiation corresponding to the X-ray beam F emitted by one of the X-ray tubes 4 will also be referred to as "primary radiation" while the photons deviated by the X-rays passing through a portion of the human body (that is, the breast) and propagating in different directions relative to the primary radiation will be referred to as "scattering radiation" or "diffuse radiation" or "secondary radiation".

Below is a detailed description of the grille 7 for removing diffuse radiation, forming part of the apparatus 1 according to the invention.

The grille 7 for removing diffuse radiation comprises a plurality of plates 26 which are positioned to face one another, that is, which are positioned in such a way that their respective large planar faces or planes 27 are opposed to each other.

It should be noted that the term "plate" is used to mean a substantially planar element characterized by a longitudinal direction, that is a direction of principal extension, a transverse direction and a thickness.

Preferably, the plates 26 are in the form of laminas (whose thickness is in the order of hundredths of a millimeter).

It should be noted that the plates 26 together define the filtering space 8.

The plates 26 converge towards the same region R1 proximal to the X-ray source (preferably towards a small-volume region).

It should be noted that in the side view of the apparatus 1 shown in FIG. 2, the plates 26 converge towards the same point of convergence FC, that is, towards the same focus.

It should also be noted that one of the tubes 4 of the apparatus 1 is positioned at the point of convergence FC, or focus (in the embodiment illustrated, the middle tube 4c).

In other words, the plates 26 are oriented in such a way that the planes 27 defined by the large faces of the selfsame plates 26 are, in use, slightly rotated about the plane T defined by the patient's chest to converge at the same point of convergence or focus FC.

Preferably, the inclination of the plates 26 is a function of their distance from the second plane 5.

More specifically, as may be observed in FIG. 2, the inclination of the planes 27 defined by the large faces relative to the plane T defined by the patient's chest increases with distance of the plate 26 from the second plane 5 (that is, the greater the distance of the plates 26 from the second plane 5, the greater the inclination, and the smaller the distance of the plates 26 from the second plane 5, the smaller the inclination).

FIG. 2 schematically illustrates a portion of the grille 7 for removing diffuse radiation forming part of the apparatus 1 according to the invention and shows a plurality of plates 26. For convenience, four of the plates are labeled individually 26a, 26b, 26c, 26d, starting from the one of the four that is furthest from the second plane 5.

It should be noted that each of the plates (26a, 26b, 26c, 26d) has its own angle of inclination ($\beta 1$, $\beta 2$, $\beta 3$, $\beta 4$) relative to the plane T defined by the patient's chest TO and that these angles of inclination ($\beta 1$, $\beta 2$, $\beta 3$, $\beta 4$) decrease, starting from the plate 26a, towards the second plane 5.

More specifically, in FIG. 2, the planes 27 defined by the large faces of the plates (26a, 26b, 26c, 26d) converge, according to the invention, at a focus point labeled FC (in three-dimensional space, that point is a straight line).

It should be noted that the grille 7 for removing diffuse radiation is a "focused" grille (that is, the plates are arranged in such a way as to converge towards the same point of convergence or focus FC).

It is stressed that one of the tubes 4 of the apparatus 1 is positioned at the point of convergence FC, or focus (preferably, the middle tube 4c).

Thus, more generally speaking and according to the invention, the plates 26 are oriented in such a way as to converge at the point of emission of one of the X-ray tubes 4.

According to the invention, the plates 26 extend along a direction of extension K substantially parallel to a plane T defined by the patient's chest TO when the patient's breast is in the positioning region R2 (that is, when the patient is in the correct position for mammography/tomosynthesis to be performed).

More generally speaking the positioning region R2 is a spatial region in which the breast can be positioned in such a way that the X-ray beams emitted by the tubes 4 can pass through it in order to perform mammography/tomosynthesis.

It should be noted that the patient is correctly positioned when she faces the second plane 5 in front of her (in FIG. 1, on the other hand, the patient is turned by 90° to the correct position, that is, she is positioned sideways relative to the second plane 5).

It should also be noted that FIG. 1 schematically illustrates a breast M which is positioned in the positioning region R2.

It should be noted, furthermore, that the direction of extension K is also substantially parallel to the second plane 5, that is, the plane in which the X-ray source/sources is/are movable, that is in which the X-ray source/sources is/are positioned.

Moreover, in the preferred embodiment, the second plane 5 is substantially at a right angle to the first plane 3.

It should be borne in mind that the plates 26 are positioned in such a way as to substantially face towards the patient's chest TO.

It should be noted that the apparatus 1 comprises movement means (not illustrated) for the grille 7 for removing diffuse radiation, by which the grille 7 is moved at least during emission of the X-ray beam.

Preferably, these movement means are configured to allow the grille 7 for removing diffuse radiation to be translated along a direction of translation C at a right angle to the direction of extension K.

It should be noted that the direction of translation C is preferably parallel to the first, detection plane 3.

Also, preferably and in the preferred embodiment illustrated in FIG. 1, the direction of translation C is a direction substantially at a right angle to the second plane 5.

Preferably, the movement means are activated to move the grille 7 for removing diffuse radiation while the mammography or even tomosynthesis is being performed in such a way as to cancel the shadow produced by the plates on the detector device 2 (and hence to reduce the artificial effect it produces on the radiographic image).

According to another aspect, the grille 7 for removing diffuse radiation is characterized by a density (that is, a number) of plates 26 along the direction C which is relatively high. Preferably, along the direction labeled C, the grille 7 for removing diffuse radiation comprises a linear plate density per linear centimeter that is substantially greater than half the linear pixel density of the detector device 2 along the same direction.

According to this aspect and more generally speaking, the grille 7 comprises, along the direction C, a number of plates 26 per centimeter which is substantially greater than half the number of pixels per centimeter of the detector device 2 along the same direction C.

The high plate density advantageously makes it possible to minimize the stroke of the grille 7 for removing diffuse radiation along the direction C needed to allow the shadow of the plates 26 in the first, detection plane 3 to be cancelled.

More specifically, the stroke needed to allow the cancellation of the shadow of the grille 7 plates is minimized so it is less than a predetermined value required by current regulations (for example, 5 mm): if the stroke needed to cancel the shadow were greater than this, the part of the breast not analyzed near the surface against which the patient's chest rests would be larger than the predetermined value (with the risk of not being able to identify lesions or tumor growths in the region in the proximity of the chest).

In this regard, current regulations (by fixing the requirements of the supporting surface and of the detecting device) limit the maximum extension in the direction at a right angle to the chest of the region of the breast that need not be subjected to analysis. The stroke necessary to enable cancellation of the plates must be less than this value, fixed by regulations.

More specifically, IEC 60601-2-45, section 203.8.5.4.101 fixes a value of less than 5 mm (and a testing method) as the requirement for the distance between the edge of the detector surface adjacent to the patient's chest and the outer edge of the breast supporting surface.

More specifically, it should be noted that a linear plate density along the direction C that is substantially greater than half the linear pixel density of the detector device 2 along the direction C makes it possible to cancel the shadow caused by the presence of the grille 7 for removing diffuse radiation with a limited grille 7 stroke.

This advantageously makes it possible to minimize the field of vision loss along the direction labeled C in FIG. 2.

For example, if the device has a pixel whose linear dimension is in the order of 0.1 mm and a plate density greater than 130 pairs per centimeter is chosen, the stroke of the grille 7 needed to correctly cancel the shadow on the image is less than two millimeters.

Alternatively, if the grille 7 for removing diffuse radiation is not equipped with a movement mechanism, it is possible to use a software filter which, if suitably configured, can cancel the shadow of the plates 26 in the first, detection plane 3.

The plates 26 are made preferably of a metal with a high atomic number, such as lead, for example, or in any case of a material capable of attenuating X-rays.

The plates 26 are configured in such a way as to allow a large fraction of the primary radiation to pass through the space 8 and to reduce the amount of secondary radiation passing through the filtering space.

The grille 7 for removing diffuse radiation therefore advantageously attenuates the secondary radiation incident upon the first, detection plane 3, and at the same time allows the primary radiation to pass through the filtering space.

It should be noted that, advantageously, the grille 7 for removing diffuse radiation of the apparatus 1 does not need to be removed during tomosynthesis and in fact considerably improves the quality of the radiographic image even during tomosynthesis.

More specifically, the grille 7 for removing diffuse radiation makes it possible, during both mammography and tomosynthesis, to increase the ratio between the contrast of the radiographic image detected with the grille 7 for removing diffuse radiation and without the grille 7.

An advantage of this invention, therefore, is that it allows both tomosynthesis and mammography to be performed without having to remove the grille 7.

It is evident, therefore, that in order to optimize the passage of the primary radiation through the grille 7, the X-ray source must be positioned at a certain distance from the detector device 2 (hereinafter, this distance is referred to as "optimum distance" between X-ray source and detector device).

It should be noted that the grille 7 allows the apparatus 1 to obtain a good quality image even if the source is not located at the optimum distance, that is to say, even if the source is further from/closer to the detector device 2 (that is, located at a distance different from the optimum distance).

In other words, the X-ray source or sources may be positioned relative to the detector device 2 within a range of distances in which the images obtained are of a good quality (this range is advantageously plus or minus 10% of the optimum distance).

According to another aspect, the detector device 2 can move relative to the at least one X-ray source 4 and supports the grille 7 in such a way that the latter can move as one with the detector device 2.

It should be noted that according to this aspect, the grille 7 is preferably movable relative to the detector device 2 along the direction C in order to allow the shadow produced in the detection plane 3 to be cancelled (as described above).

Preferably, therefore, the grille 7 is movable as one with the detector device 2 and is movable relative to the detector device 2 in order to allow the shadow produced in the detection plane 3 to be cancelled.

The invention described is susceptible of industrial application and may be modified and adapted in several ways without thereby departing from the scope of the inventive concept. Moreover, all details of the invention may be substituted for technically equivalent elements.

What is claimed is:

1. An apparatus for performing at least one chosen from tomosynthesis and mammography of a breast of a patient, comprising:

an X-ray detector device, designed to receive and detect X-rays in a first, detection plane, the X-ray detector device comprising a plurality of pixels;
an X-ray source, which can be activated individually and which is positioned to emit a corresponding beam of X-ray towards the first, detection plane;
a region for positioning the breast in such a way that the breast intercepts the beam from the X-ray source;
a processing and control unit, connected to the X-ray source for activating the X-ray source and connected to the X-ray detector device for receiving a signal relating to the X-rays which pass through the breast and are detected by the X-ray detector device, the unit being constructed and arranged to derive from the signal, a radiographic image representative of an internal structure of the breast of the patient;
a grille for removing diffuse radiation, the grille being interposed between the positioning region and the X-ray detector device so that the X-rays which pass through the breast pass through the grille, the grille comprising a plurality of plates which are positioned opposite a chest of the patient when the breast is positioned in the positioning region, the plates being angled to converge towards a region proximal to the X-ray source, the grill also comprising, in a direction which is substantially at a right angle to a direction of extension of the plates, a number of plates per centimeter which is greater than half of a number of the pixels of the X-ray detector device per centimeter in the direction which is substantially at a right angle to the direction of extension of the plates;
wherein the X-ray source can move with respect to the X-ray detector device in a second plane and wherein the plates extend in a direction of extension substantially parallel with the second plane;
wherein an angle of orientation of the plates increases with a distance of the plates from the second plane.

2. The apparatus according to claim 1, comprising a plurality of X-ray sources which are positioned along the second plan.

3. The apparatus according to claim 1, wherein the second plane is substantially at a right angle to the first, detection plane.

4. The apparatus according to claim 1, wherein the second plane is substantially parallel with a plane defined by the chest of the patient when the breast is positioned in the positioning region.

5. The apparatus according to claim 1, wherein the plates extend in a direction of extension substantially parallel with a plane defined by the chest of the patient when the breast is positioned in the positioning region.

6. The apparatus according to claim 1, comprising a movement mechanism for moving the grille during emission of the X-ray beam.

7. The apparatus according to claim 6, wherein the movement mechanism moves the grille in a direction of movement substantially at the right angle to the direction of extension of the plates.

8. The apparatus according to claim 6, wherein the direction of movement is at a right angle to a plane defined by the chest of the patient.

9. The apparatus according to claim 1, comprising a first frame having the shape of a ring and supporting the X-ray source and the X-ray detector device.

10. The apparatus according to claim 9, comprising a second frame and in which the first frame is rotatably supported by the second frame.

11. The apparatus according to claim 10, comprising a movement mechanism for vertical movement of the first frame relative to the second frame.

12. The apparatus according to claim 9, wherein the first frame can rotate about a center of the ring.

13. The apparatus according to claim 1, wherein the X-ray detector device can move relative to the X-ray source and supports the grille in such a way that the grille can move as one with the X-ray detector device during movement of the X-ray detector device relative to X-ray source.

14. An apparatus for performing at least one chosen from tomosynthesis and mammography of a breast of a patient, comprising:
- an X-ray detector device, designed to receive and detect X-rays in a first, detection plane, the X-ray detector device comprising a plurality of pixels;
- an X-ray source, which can be activated individually and which is positioned to emit a corresponding beam of X-rays towards the first, detection plane;
- a region for positioning the breast in such a way that the breast intercepts the beam from the X-ray source;
- a processing and control unit, connected to the X-ray source for activating the X-ray source and connected to the X-ray detector device for receiving a signal relating to the X-rays which pass through the breast and are detected by the X-ray detector device, the unit being constructed and arranged to derive from the signal, a radiographic image representative of an internal structure of the breast of the patient;
- a grille for removing diffuse radiation, the grille being interposed between the positioning region and the X-ray detector device so that the X-rays which pass through the breast pass through the grille, the grille comprising a plurality of plates which are positioned opposite a chest of the patient when the breast is positioned in the positioning region, the plates being angled to converge towards a same region proximal to the X-ray source, the grill also comprising, in a direction which is substantially at a right angle to a direction of extension of the plates, a number of plates per centimeter which is greater than half of a number of the pixels of the X-ray detector device per centimeter in the direction which is substantially at a right angle to the direction of extension of the plates;
- a plurality of X-ray sources which are positioned along a second plane and wherein the plates extend in a direction of extension substantially parallel with the second plane.

* * * * *